(12) United States Patent
Frank et al.

(10) Patent No.: US 7,896,900 B2
(45) Date of Patent: Mar. 1, 2011

(54) MEDICAL INSTRUMENT FOR GRASPING AN OBJECT, IN PARTICULAR NEEDLE HOLDER

(75) Inventors: Timothy Graham Frank, Wormit Newport-On-Tay Fife (GB); J. Duncan S. Martin, Dundee (GB); Ian Rutherford, Dundee (GB); Stuart I. Brown, St. Andrews Fife (GB); James Gove, Dundee (GB); Leslie Kelly, Cupar (GB)

(73) Assignee: University of Dundee (GB)

( * ) Notice: Subject to any disclaimer, the term of this patent is extended or adjusted under 35 U.S.C. 154(b) by 550 days.

(21) Appl. No.: 11/771,124

(22) Filed: Jun. 29, 2007

(65) Prior Publication Data

US 2008/0188891 A1    Aug. 7, 2008

(30) Foreign Application Priority Data

Jun. 29, 2006    (EP) .................................... 06013422

(51) Int. Cl.
*A61B 17/00* (2006.01)
(52) U.S. Cl. ........................................................ 606/208
(58) Field of Classification Search .......... 606/205–208; 81/342, 64, 90.2, 345, 418, 176.3, 119, 318–330; 600/51, 104, 141
See application file for complete search history.

(56) References Cited

FOREIGN PATENT DOCUMENTS

FR    575948 A    8/1924

OTHER PUBLICATIONS

Extended European Search Report; EP 09 16 8245; Nov. 25, 2009; 7 pages.

*Primary Examiner* — Todd E Manahan
*Assistant Examiner* — Christopher Schubert
(74) *Attorney, Agent, or Firm* — St. Onge Steward Johnston & Reens LLC

(57) ABSTRACT

A medical instrument for grasping an object, in particular a surgical needle holder, including an elongated shaft, two jaw parts arranged at a distal end of the shaft, at least one of the jaw parts being pivotable with respect to the other of the jaw parts between a grasp state for grasping the object between the jaw parts and a release state for releasing the object. A handle is arranged at a proximal end of the shaft and has at least one operating element for moving the at least one pivotable jaw part between the grasp state and the release state via an axially movable force transmission element operatively connected with the at least one operating element and with the at least one pivotable jaw part via an articulated joint. The instrument further includes a latching mechanism for immobilizing the at least one pivotable jaw part in the grasp state.

31 Claims, 12 Drawing Sheets

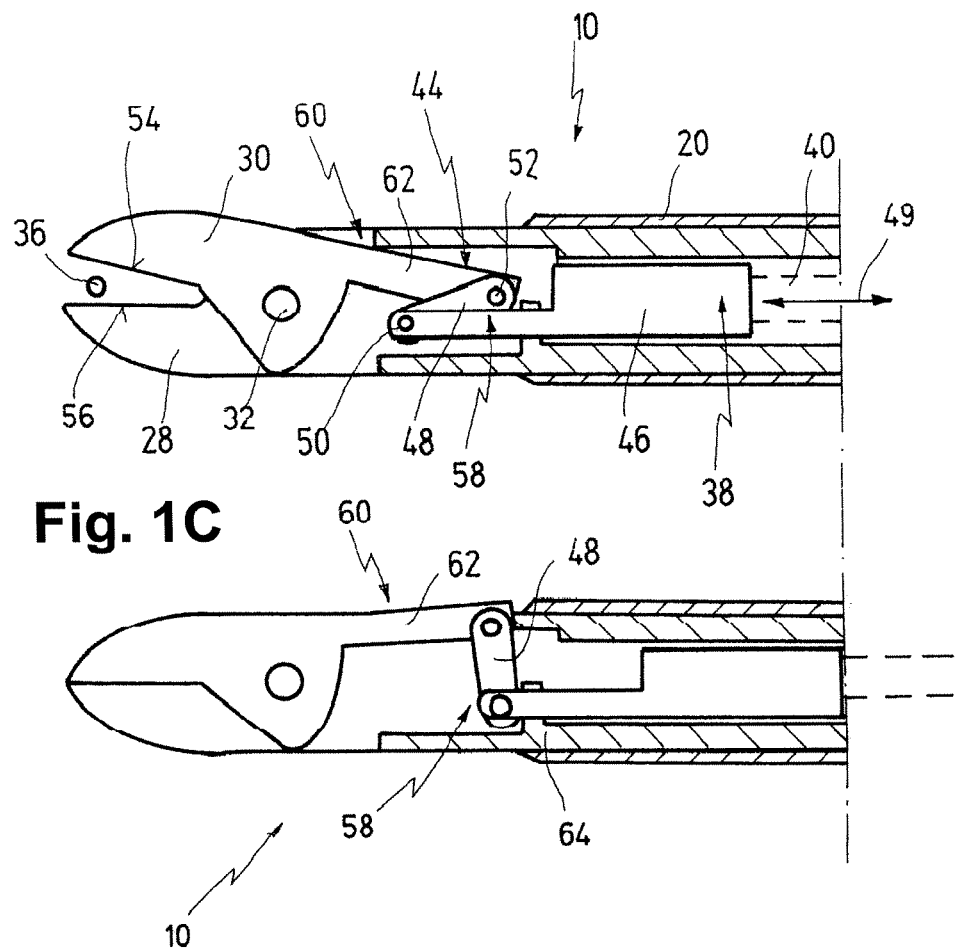
Fig. 1C
FIG. 1E
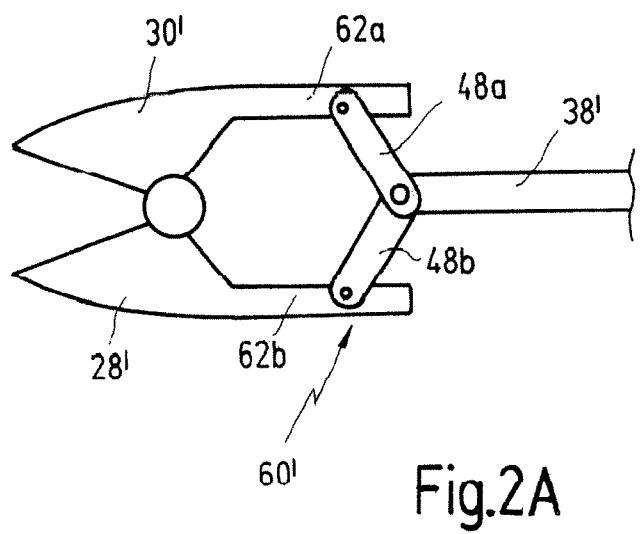
Fig. 2A

MEDICAL INSTRUMENT FOR GRASPING AN OBJECT, IN PARTICULAR NEEDLE HOLDER

CROSS-REFERENCE TO RELATED APPLICATIONS

The present application claims priority of European Patent Application No. 06 013 422.8 filed on Jun. 29, 2006.

BACKGROUND OF THE INVENTION

The invention generally relates to medical instruments which are suited for grasping objects. More specifically, the invention relates to surgical needle holders.

A needle holder is, for example, known from the firm catalogue "Storz Karl Storz—Endoskope, Volume Laparoscopy, 4. Edition January 2002, Pages NH 1, NH 2 C, NH 3 C, NH4C, NH5C, NH6C, NH7C and NH8B.

While the present invention will be hereinafter described with respect to a medical instrument for grasping a surgical needle, wherein in such case the instrument is also referred to as a needle holder, the invention is not restricted to such an application and other applications are also conceivable. For example, the medical instrument can be used for grasping an implant, for example a bone screw or a bone nail or the like.

In case of use of a medical instrument mentioned at the outset as a surgical needle holder, a needle can be grasped between the two jaw parts for performing a suturing or ligature operation in the human or animal body.

The needle holders known from the above-mentioned firm catalogue each comprise an elongated shaft, two jaw parts arranged at the distal end at the shaft, and a handle arranged at the proximal end of the shaft. At least one of the jaw parts is pivotable with respect to the other jaw part. The handles of these known instruments comprise two grip parts, one of which is movable and serves as the operating element for moving the pivotable jaw part. Force transmission from the operating element to the pivotable jaw part is accomplished by an axially movable force transmission element, which is configured as a push/pull rod or wire.

In order to facilitate use of the instrument, the known needle holders comprise a latching mechanism for immobilizing the pivotable jaw part in the grasped state, in which the needle must be securely grasped between the jaw parts so as to not drop from the needle holder. The latching mechanism of the known needle holders comprises a ratchet which immobilizes the operating element, i.e. in case of the known needle holders the movable grip part or in case that both grip parts are movable, both grip parts with respect to one another. Other latching mechanisms which are known heretofore comprise an element which engages the force transmission element itself, thus blocking the axial moveability of the force transmission element in the grasped state.

The known medical instruments have the drawback that, besides the degree of freedom of closing and opening the jaw parts, they have no further degrees of freedom or achieve these only with high friction or additional transmission means due to the fact that the latching mechanism of the known medical instruments is arranged in the handle of these instruments and immobilizes the operating element for closing and opening the jaw parts or the force transmission element itself. For example, rotating the jaw parts with respect to the shaft is not possible. For, when the operating element is immobilized, the force transmission element and the jaw part, are also blocked against any further movement with respect to the shaft. A rotation of the jaw parts with respect to the shaft is not possible. Rotation of the jaw parts is only possible by rotating the whole instrument about its longitudinal axis, which is, however, cumbersome.

SUMMARY OF THE INVENTION t is an object to improve a medical instrument of the kind mentioned at the outset such that the afore-mentioned drawbacks are avoided, in particular that the instrument can be provided with additional degrees of freedom for the two jaw parts.

According to a first aspect of the invention, a medical instrument for grasping an object is provided, comprising an elongated shaft having a distal end and a proximal end, two jaw parts arranged at the distal end of the shaft, at least one of the two jaw parts being pivotable with respect to the other of the two jaw parts between a grasp state for grasping the object between the two jaw parts and a release state for releasing the object. A handle is arranged at the proximal end of the shaft and has at least one operating element for moving the at least one pivotable jaw part between the grasp state and the release state. An axially movable force transmission element has a first end operatively connected with the at least one operating element, and a second end connected with the at least one pivotable jaw part via an articulated joint. A latching mechanism for immobilizing the at least one pivotable jaw part in the grasp state is provided, the latching mechanism comprising at least one latching element arranged in the region of the force transmission from the force transmission element to the at least one pivotable jaw part which, when the force transmission element is further axially moved beyond a position in which the grasp state is reached, changes into an over-center stable state.

According to a second aspect of the invention, a medical instrument for grasping an object is provided, comprising an elongated shaft having a distal end and a proximal end, two jaw parts arranged at the distal end of the shaft, at least one of the two jaw parts being pivotable with respect to the other of the two jaw parts between a grasp state for grasping the object between the two jaw parts and a release state for releasing the object. A handle is arranged at the proximal end of the shaft and has at least one operating element for moving the at least one pivotable jaw part between the grasp state and the release state. An axially movable force transmission element has a first end operatively connected with the at least one operating element, and a second end connected with the at least one pivotable jaw part via an articulated joint. A latching mechanism for immobilizing the at least one pivotable jaw part in the grasp state is provided. The jaw parts are rotatable relative to the shaft about a longitudinal axis of the shaft, and the force transmission element further is rotatable about a longitudinal axis of the force transmission element and rotationally fixedly connected with the at least one pivotable jaw part.

In contrast to the known medical instruments, the medical instrument according to the present invention is based on the concept to provide the latching mechanism for immobilizing the at least one pivotable jaw part in the region of the force transmission from the force transmission element to the pivotable jaw part.

Further, the latching mechanism of the instrument according to the invention comprises at least one latching element which changes into an over-centre state when the force transmission element is further axially moved beyond the position in which the grasped state is reached. The at least one latching element immobilizes the pivotable jaw part when it is in the over-centre stable state.

Due to the fact that the latching function is realized in the region of the force transmission from the force transmission element to the at least one pivotable jaw part instead of being realized in the handle, the force transmission element can take over further functions of movement of parts of the instrument; in particular, as provided in a preferred refinement of the invention, it can be used to rotate the jaw parts about the longitudinal axis relative to the shaft. According to the invention, due to an absence of tension in the force transmission element, friction that would otherwise occur, is removed from the force transmission element.

In a preferred embodiment, the at least one latching element is elastically deformable and changes into the over-centre stable state via a deformed state.

An advantage of the provision of an elastically deformable latching element is that the force exerted by the jaw parts on the object grasped between the jaw parts is, on the one hand, sufficient to securely hold the object between the jaw parts, while, on the other hand, the risk of damaging the object by exerting an excessive grasping force on the object is lowered, because further axially moving of the force transmission element is "distributed" by the deformation of the latching element when the grasped state of the jaw parts is reached.

It is to be understood that the grasped state depends on the size of the object to be grasped between the jaw parts and its position between the jaw parts in terms of the longitudinal extension of the jaw parts and can correspond to different relative positions between the two jaw parts.

In a further preferred refinement, the at least one latching element forms at least part of the articulated joint and/or of a proximal portion of the at least one movable jaw part and/or of the distal portion of the force transmission element.

The provision of the at least one latching element at least as part of the force transmission path itself has the advantage that the latching mechanism is very simple in terms of construction, and, in particular, does not require additional parts.

In a further preferred refinement, the at least one latching element changes into its unlatched state when the force transmission element is moved back beyond the position in which the grasped state is reached.

The advantage of this measure is that the latching mechanism and thus the pivotable jaw part is unlocked from its immobilized state by simply operating the operating element so as to move the force transmission element in the direction opposite to the direction for latching the pivotable jaw part.

In order to enhance the operational safety of the instrument, provisions can be made, for example by providing recesses or windows in the region of the distal portion of the shaft, in order to have an access to the distal end of the force transmission element or the articulated joint by an auxiliary instrument to release the latching mechanism. For example, in case the force transmission element breaks in a proximal portion, the auxiliary instrument can be brought through the access to the latching element for releasing the latched state so that the object can be freed from the jaw parts.

In a further preferred refinement, the articulated joint comprises a lever one end of which is articulatedly connected with the force transmission element at a first location, and the other end of which is articulatedly connected with the at least one pivotable jaw part at a second location which is spaced apart from the first location in direction transverse to the direction of axial movement of the force transmission element, wherein in the release state one of the first and second locations is positioned distally from the other location, and the latching element changes into the stable state, when the location which is the distal one in the release state moves in a position which is proximally from the other location, or vice versa.

In this refinement, the at least one elastically deformable latching element changes into the stable state by an over-centre-movement of the lever of the articulated joint. An advantage of this configuration is that the user of the instrument obtains a tactile feedback of the transition of the latching element from the unlatched in the latched state, because the user feels a force maximum when the first and second locations are in approximately the same position with respect to the longitudinal direction of the force transmission element and, when moving the force transmission element by means of the operating element slightly further, the force felt by the user remarkably decreases, because the latching element changes into the stable state.

In further preferred refinements, the proximal portion of the at least one moveable jaw part forms the latching element and is elastically deformable, for example, configured as a leaf spring, and/or the lever of the articulated joint forms the deformable element.

In connection with the latter refinement, the lever is configured in arch-shape, in particular in about C-shape, the first and second locations of the articulated connection with the force transmission element and the at least one movable jaw part being arranged at least approximately at the end of the arch. The design of a leaf spring is only one of several designs of an elastically deformable element, which can be used in the latching mechanism according to the invention.

The afore-mentioned preferred configuration has the advantage of a constructively simple design.

In a further preferred refinement, the jaw parts are rotatable relative to the shaft about a longitudinal axis of the shaft.

As already mentioned before, this particular advantageous refinements has been made possible by the configuration of the latching mechanism according to the invention, because the force transmission element itself is not immovably blocked in the latching state by engagement with another part and can be rotated in frictionless manner. The rotatability of the jaw parts has the advantage that the object, in particular a needle, can be oriented at the surgical site in a variety of positions without necessitating to rotate the whole instrument. Thus, the jaw parts have one, two or more additional degree(s) of freedom of movement relative to the shaft besides the opening and closing movement.

In this connection, it is preferred, if the force transmission element further is rotatable about a longitudinal axis thereof and rotationally fixedly connected with the at least one pivotable jaw part.

The advantage of this measure is that opening and closing the jaw parts as well as rotating the jaw parts can be accomplished by one and the same force transmission element. Thus, the number of parts of the instrument is advantageously not increased although the number of degrees of freedom of movement is increased.

It is to be understood that the afore-mentioned refinement and the refinement mentioned before that are considered each as inventions independent from the features of the characterizing portion of claim 1.

In a further preferred refinement, the force transmission element comprises a helix or coil.

A force transmission element comprising a helix or coil is particularly advantageous in case that the jaw parts are rotatably relative to the shaft; because of its larger diameter, a helix or coil can transmit higher torques than a thin rod or wire.

In this connection, it is preferred, if the helix or coil does not lengthen when transmitting pull forces, and/or does not shorten when transmitting push forces.

This measure has the advantage that the helix or coil not only can transmit torques, but can also reliably transmit pull and push forces for opening and closing and, in particular, latching the at least one pivotable jaw part.

In a further preferred refinement, the helix or coil is configured as a twisted strip.

A twisted strip has the advantage that it can transmit pull and push forces as well as torques to the jaw parts.

In a very simple preferred refinement the force transmission element comprises a push/pull rod.

According to a further preferred refinement, the force transmission element comprises a helix or coil which is cored with the afore-mentioned push/pull rod.

Such a design of a force transmission element is particularly suited as an element for transmitting torques as well as push and pull forces.

In particular, it is preferred, if the push/pull rod is made in one piece with the helix or coil.

The one-piece configuration of the push/pull rod with the helix or coil has the further advantage, that the push/pull rod increases the stability of the helix or coil against twisting when transmitting high torques.

In a further preferred refinement, the at least one operating element is movable in longitudinal direction of the shaft for axially moving the force transmission element.

Contrary to the known needle holders which comprise a pivotable or two pivotable grip elements forming the handle, and which comprise the latching mechanism in form of a ratchet between the grip elements, the medical instrument according to the invention uses the concept of a slider for axially moving the force transmission element.

The operating element can be configured as a knob which can be operated by the thumb or a finger of the hand holding the instrument. Thus, a one-hand operation is possible as it is the case in the known instruments for closing and opening jaw parts.

In a further preferred refinement, the at least one operating element is rotatable about the longitudinal direction of the shaft for rotating the force transmission element.

In connection with the afore-mentioned refinement, the operating element can be advantageously configured as a rotatable knob, for example a wheel suited for one-hand operation. One and the same operation element, thus, is operable for closing and opening and latching the jaw parts, and also for rotating the jaw parts relative to the shaft even when the jaw parts are latched in the grasped state, because the operating element itself is not blocked against movement.

In a further preferred refinement, the shaft has a distal end portion and a main portion, wherein the jaw parts are arranged at the distal end portion, and the distal end portion is inclinable with respect to the main portion of the shaft.

The advantage of this measure is a further enhancement of the number of degrees of freedom of movement of the jaw parts and thus of the object held between the jaw parts.

The number of degrees of freedom of the jaw parts and, thus, an object held between the jaw parts is still further increased, if the shaft is rotatable about its longitudinal axis.

In connection with the afore-mentioned refinement, the jaw parts and, thus, an object held between the jaw parts can be positioned and oriented in a large range of spatial and solid angle coordinates, in particular when the jaw parts, in addition, are rotatable relative to the shaft. When reference is made to a rotation of the shaft about its longitudinal axis in the present description, this is meant to be understood as a rotation about the longitudinal axis of the main portion (proximal portion) of the shaft in cases where the distal portion of the shaft is inclinable with respect to the main portion of the shaft.

In case of the rotatability of the jaw parts relative to the shaft, the jaw parts are preferably rotatable about a longitudinal direction of the distal end portion and relative thereto.

Preferably, a second axially movable force transmission element is provided which is operatively connected with the distal end portion of the shaft and with a second operating element arranged at the handle.

The provision of a second axially movably force transmission element has the advantage that the action of inclining the distal end portion with respect to the main portion of the shaft can be operated independently from the actions of closing, opening and latching as well as rotating the jaw parts relative to the distal end portion.

Preferably, the shaft is rotatably fixed to the distal end portion of the shaft.

In a further preferred refinement, a third operating element is arranged at the handle for rotating the shaft.

In the simplest case, the shaft can be provided with a rotating knob in the proximal end portion of the shaft in next vicinity to the handle in order to enabling a onehand operation of the third operating element, too.

In a further preferred refinement, the handle comprises an elongated bar.

A handle comprising an elongated bar is ergonomically advantageous, because it can be held in the palm of the hand leaving the thumb and fingers free for operating the first operating element and, if present, the second and third operating element, too, wherein all operations can be performed in one-hand operation.

For improving the ergonomy, it is preferred if the handle is inclinable with respect to the longitudinal direction of the shaft.

By inclining the handle with respect to the longitudinal direction of the shaft, the handle can be held like a pistol handle.

In connection with the configuration of the handle comprising a bar, it is preferred, if the first operating element, the second operating element and the third operating element are arranged at the handle in a serial order in longitudinal direction of the shaft.

By virtue of this arrangement of the operating element, each of them can be operated by the thumb or fingers of the same hand holding the instrument.

Further features and advantages will become apparent from the following description and the accompanying drawings.

It is to be understood that the features mentioned before and those features still to be explained below are not only applicable in the combinations given, but also in other combinations or in isolation without departing from the scope of the invention.

BRIEF DESCRIPTION OF THE DRAWINGS

Exemplary embodiments of the invention are shown in the drawings and will be described hereinafter with respect thereto. In the drawings:

FIGS. 1C-1F show schematic representations of the distal portion according to FIG. 1B in a longitudinal section showing the principles of a latching mechanism for immobilizing a pivotable jaw part of the instrument in the grasp state;

FIG. 2A shows a schematic representation of another embodiment of a latching mechanism;

DETAILED DESCRIPTION OF THE INVENTION

Figure 1A:
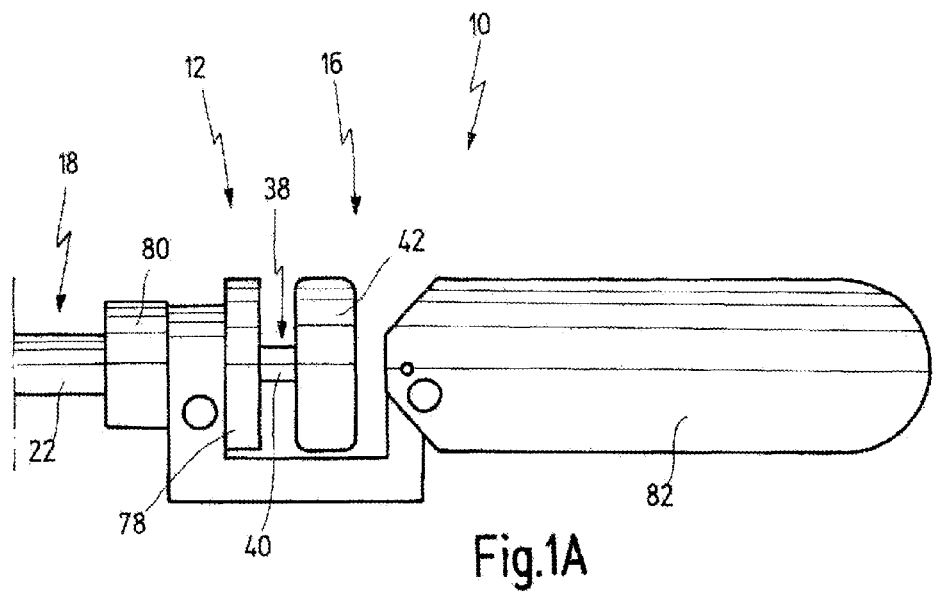
FIG. 1A shows a schematic representation of a proximal portion of a medical instrument for grasping an object in a side view.
Figure 1B:
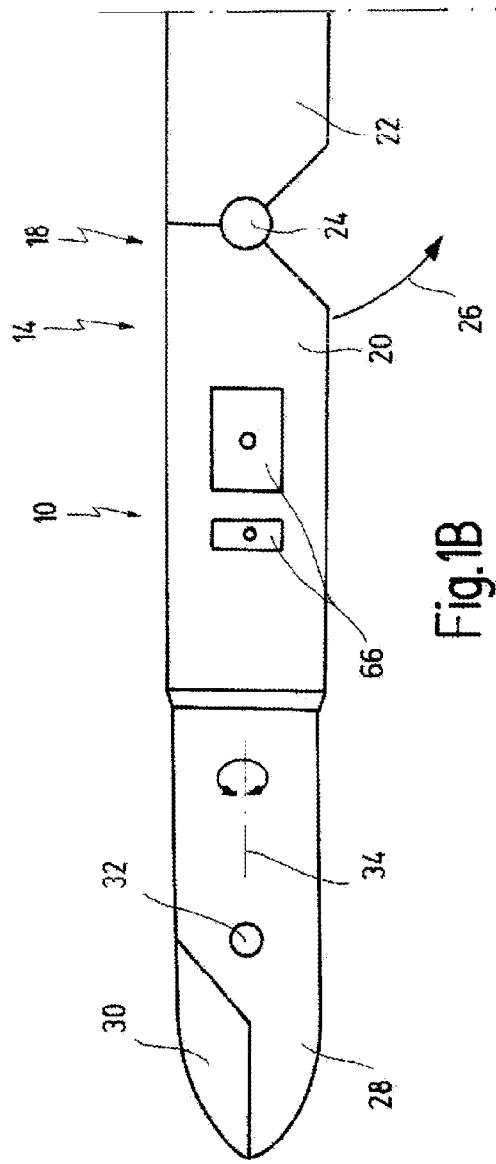
FIG. 1B shows a distal portion of the medical instrument in FIG. 1A in an enlarged scale with respect to FIG. 1A in a side view.

FIGS. 1A and 1B together show a medical instrument for grasping an object, which is generally labeled with reference numeral 10. The medical instrument, in particular, is a surgical needle holder, i.e. the object which can be grasped with the instrument 10 is a surgical needle used in surgery for suturing or ligature operations.

FIG. 1A shows a proximal portion 12 of the instrument 10, and FIG. 1B a distal portion 14 of the instrument 10.

In the proximal portion 12, the instrument 10 comprises a handle 16 which will be described later.

An elongated shaft 18 extends from the handle 16 to the distal portion 14 of the instrument 10. It is to be understood that the shaft 18 has a total length which is larger than the length shown in FIGS. 1A and 1B.

While the shaft 18 is straight in the embodiment shown, the shaft 18 can also have a curvature in a portion between the distal portion 14 and the proximal portion 12 of the instrument.

The shaft 18 further comprises a distal end portion 20 which is inclinable with respect to a main portion 22 of the shaft. To this end, the distal end portion 20 is connected with the main portion 22 via an articulation 24, an articulation axis of which extends transversely with respect to the longitudinal direction of the shaft 18. FIG. 1B shows the distal end portion 20 in straight prolongation of the main portion 22. The distal end portion 20 can be inclined with respect to the main portion 22 according to an arrow 26 in FIG. 1B.

At a distal end of the distal end portion 20, an immovable jaw part 28 and a movable jaw part 30 are arranged. The movable jaw part 30 is pivotable via an articulation 32 with respect to the immovable jaw part 28. An articulation axis of the articulation 32 runs transversely to the longitudinal direction of the shaft 18.

Further, the jaw parts 28 and 30 are together rotatable about a longitudinal axis 34 of the distal end portion 20 relative to the distal end portion 20 and, thus, relative to the shaft 18 in any angular position of inclination of the distal end portion 20 relative to the main portion 22 of the shaft 18.

With respect to FIGS. 1C through 1F, a mechanism for moving the pivotable jaw part 30 is described in more detail.

Figure 1D:
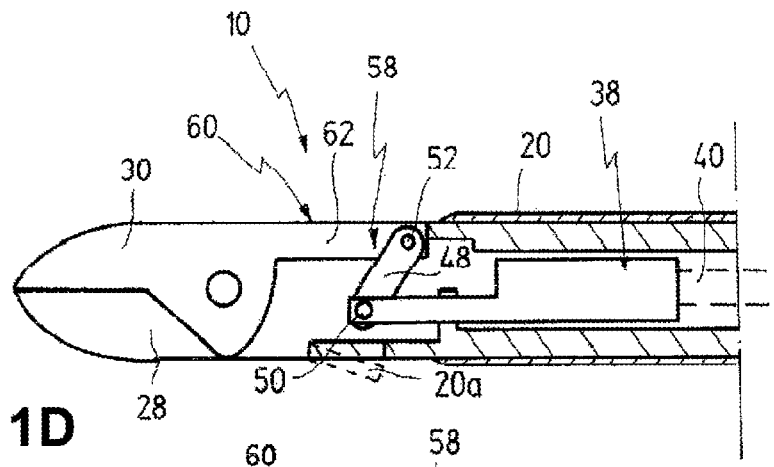
Figure 1F:
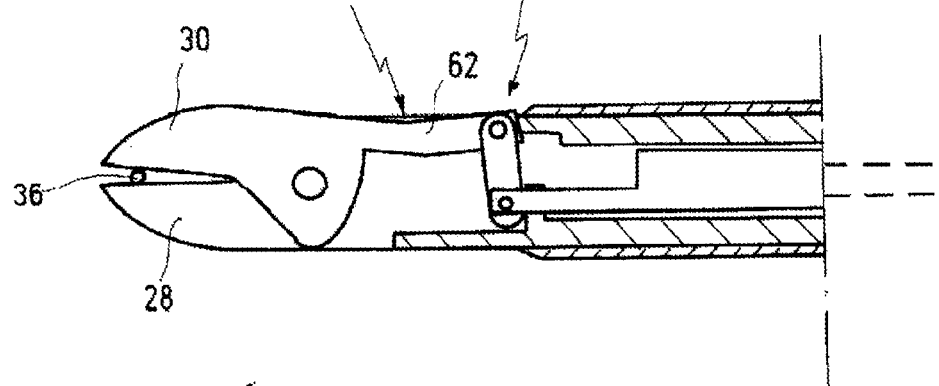

The pivotable jaw part 30 is movable between a grasp state shown in FIGS. 1D, 1E and 1F and a release state shown in FIG. 1C. In FIG. 1F an object 36, in particular a needle (shown in cross section), is grasped between the jaw parts 28 and 30 so that the jaw parts 28 and 30 are not completely closed, and FIGS. 1D and 1E show the jaw parts 28 and 30 in another grasp state, where the jaw parts 28 and 30 are completely closed. The completely closed state according to FIGS. 1D and 1E as well as the not completely closed state according to FIG. 1F where the object 36 is held between the jaw parts 28 and 30, is referred to as the "grasp state" in the present description including the claims.

FIG. 1C shows a release state, which means that the object 36 is not fixedly held between the jaw parts 28 and 30 so that the jaw parts 28 and 30 can be withdrawn from the object 36 or the object 36 can be withdrawn from the jaw parts 28 and 30, or the jaw parts 28 and 30 can be brought into engagement with the object 36.

For moving the pivotable jaw part 30 between the release state and the grasp state, a force transmission element 38 is provided which extends through the shaft 18 and is, in the simplest case, configured as a push/pull rod 40. Other embodiments of the force transmission element 38 will be described later.

The force transmission 38 is operatively connected with an operating element 42 arranged at the handle 16 of the instrument 10. At the distal end, the force transmission element 38 is operatively connected with the pivotable jaw part 30 via an articulated joint 44. In more detail, the force transmission element 38 comprises a distal end portion 46 which is articulatedly connected with a lever 48 of the articulated joint 44 at a first end of same, and the other of the lever 48 is articulatedly connected with the pivotable jaw part 30.

The force transmission element 38 is axially movable in longitudinal direction of the shaft 18 according to a double arrow 49 in FIG. 1C.

In the release state of the jaw part 30, a location 50 where the force transmission element 38 is articulatedly connected with the lever 48 is positioned distally from a second location 52 where the lever 48 is articulatedly connected with the jaw part 30.

The operating element 42 at the handle 16 is movable in longitudinal direction of the shaft 18 for axially moving the force transmission element 38 according to the double arrow 49.

Starting from FIG. 1C which shows the pivotable jaw part 30 in the release state, an axially movement of the operating element 42 in proximal direction causes the force transmission element 38 to axially move in proximal direction, too, thus causing the pivotable jaw part 30 to pivot about the articulation 32 and causing a grasped surface 54 of the movable jaw part 30 to approach a corresponding grasping counter surface 56 of the immovable jaw part 28. When no object is positioned between the surfaces 54 and 56, a continuous axial movement of the force transmission element 38 in proximal direction causes the pivotable jaw part 30 to completely close to the immovable jaw part 28 as shown in FIG. 1D.

Thus, at the instant when the pivotable jaw part 30 just comes into the closed state, according to FIG. 1D, the first location 50 is still positioned distally from the second location 52. In order to immobilize the pivotable jaw part 30 in the grasped state, a latching mechanism 58 is provided which immobilizes the pivotable jaw part 30 in the grasped state.

The latching mechanism 58 comprises at least one preferably elastically deformable latching element 60 which is arranged in the region of the force transmission from the force transmission element 38 to the pivotable jaw part 30, and which latching element 60 changes into an over-centre stable state when the force transmission element 38 is further axially moved beyond a position in which the grasp state is reached.

In the embodiment shown in FIGS. 1 through 5, the latching element 60 forms part of a proximal portion 62 of the pivotable jaw part 30 which proximal portion 62 is configured, for example, as a leaf spring or the like.

In other embodiments, the at least one latching element can form at least part of the articulated joint 58 or of the distal portion 46 of the force transmission element 38, or a plurality of latching elements can be provided which can form part of the articulated joint, of the proximal portion of the movable jaw part or of the distal portion of the force transmission element or any combinations thereof.

By further axially moving the operating element 42 in proximal direction, the force transmission element 38 pulls the first location 50 of the lever 48 in proximal direction until the first location 50 is positioned proximally from the second location 52. This over-centre-movement of the lever 48 causes the latching element 60 in form of the proximal portion 62 of the pivotable jaw part 30 to elastically deform as shown in FIG. 1E. In this state, the pivotable jaw part 30 is latched in the grasp state. A stop 64 prevents the force transmission element 38 from further axial movement in proximal direction. The latching element 60 now is in a deformed stable state.

FIG. 1F shows the case where the object 36 is grasped between the jaw parts 28 and 30 wherein the pivotable jaw part 30 again is latched by the latching element 60 in the grasp state. Since the jaw parts 28 and 30 are not completely closed when the object 36 is grasped between them, the latching element 60 exhibits a stronger elastic deformation in comparison with the case of FIG. 1E where no object is grasped between the jaw parts 28 and 30. The degree of deformation will depend on the thickness of the object 36 to be grasped and of the axial position of the object 36 between the jaw parts 28 and 30.

In order to bring the pivotable jaw part 30 into the release state again, departing from the state according to FIG. 1E or 1F, the operating element 42 is moved in distal direction, whereby the force transmission element 38 is moved in distal direction, too. The force transmission element 38 pushes the lever 48, i.e. the first articulation location 50 in distal direction whereby the latching element 60 can transit from the deformed into the unlatched state again.

Again referring to FIG. 1D, the latching mechanism 58 can be refined as follows. A distal portion 20*a* of the distal end portion 20 of the shaft 18 can be separated from the remaining portion of the distal end portion 20 such that it can elastically bend as shown in FIG. 1D by broken lines when the lower end of the lever 48, during its movement from the position shown in FIG. 1C to the position shown in FIG. 1F, abuts on the portion 20*a*. Thus, the portion 20*a* acts as a leaf spring at the position where the lever 48 abuts on the portion 20*a* during closing the jaw parts 28, 30. The proximal portion 62 of the jaw part 30, the lever 48, the portion 20*a* of the distal end portion 20 of the shaft 18 and, if necessary the distal end of the force transmission element 38 can contribute to the latching action in spring-like fashion.

Figure 4:
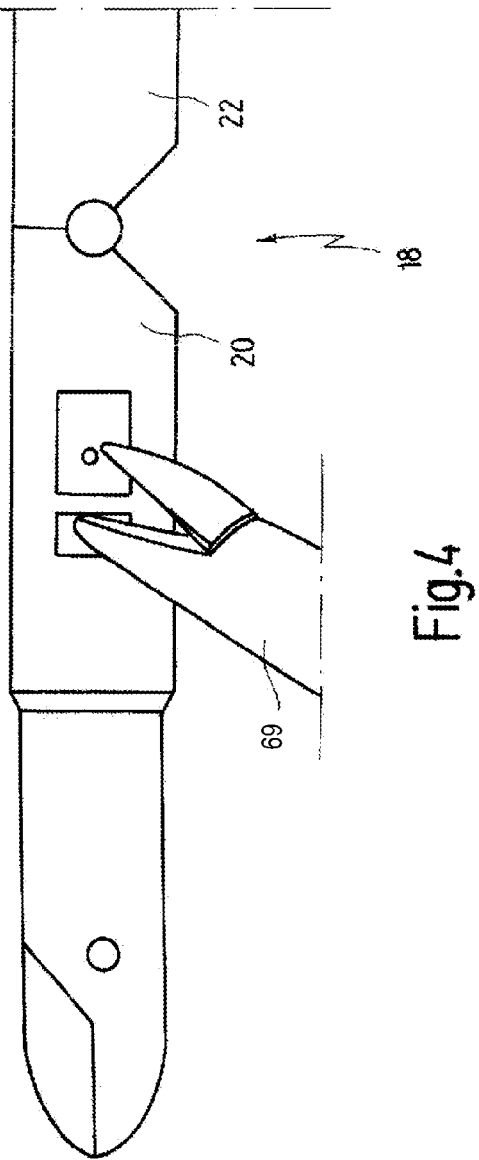
FIG. 4 shows a representation similar to FIG. 1B illustrating another detail of the distal portion of the medical instrument.

In order to enhance the operational safety of the instrument 10, one or several windows 66, in the present embodiment two windows 66, are provided in the shaft 18, here in the distal end portion 20 of the shaft 18 in order to provide an access to the force transmission element 38 and/or the articulated joint 44 for releasing the latching mechanism 44 by means of another tool or instrument 69 shown in FIG. 4. In case that, for example, the force transmission element 38 is broken so that the latching mechanism can no longer be released from the state according to FIGS. 1E or 1F by moving the operating element 42, the instrument 68 can be used to release the latching mechanism.

For this purpose, features, like one or several pins, may be provided, for example on distal end portion 46 of force transmission element 38 and/or on lever 48, which are positioned such that they are accessible through windows 66, and which can be engaged by the instrument 68 for releasing the latching mechanism.

Further, windows 66 provide an access for cleaning of the mechanism.

FIG. 2A shows another embodiment, wherein the latching mechanism 60' comprises two latching levers 48*a*, 48*b*, cooperating with proximal portions 62*a* and 62*b* of the jaw parts 28', 30', and which are connected with the force transmission element 38'. The levers 48*a*, 48*b* are connected with the proximal portions 62*a* and 62*b* in axially non displaceable and pivotable fashion.

Further, while it is described with respect to FIGS. 1C-1F that the latching mechanism 60 is engaged by pulling the force transmission element 38, and disengaged by pushing the force transmission element 38, the mechanism can be configured the opposite way, i.e. is engaged by pushing and disengaged by pulling the force transmission element 38.

Figure 2B:
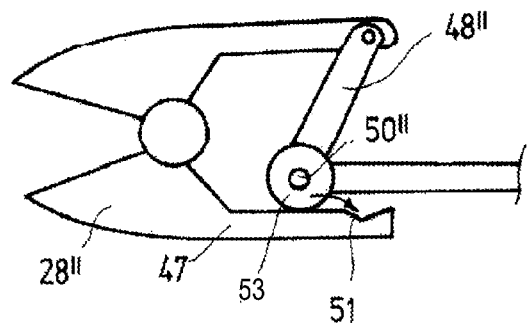
FIG. 2B shows a schematical representation of still another embodiment of a latching mechanism.

FIG. 2B shows a further embodiment, where the lever 48" is provided with a wheel 53 which slides along a surface of a proximal portion 47 of the jaw part 28" in order to reduce friction. The wheel 53 uses the pin 50" as axle. Furthermore, a groove or shallow recess 51 can be provided as a feel feed-back that the lever 48" has reached the over-centre position, in which the latching mechanism is latched.

As noted above, the jaw parts 28 and 30 are rotatable with respect to the shaft 18 about the longitudinal axis 34. To this end, the operating element 42 is configured not only for an axial movement in the direction of the longitudinal axis 34, but is also rotatable. In particular, the operating element 42 is configured as a rotatable knob or wheel as shown in FIG. 1A.

Figure 3:
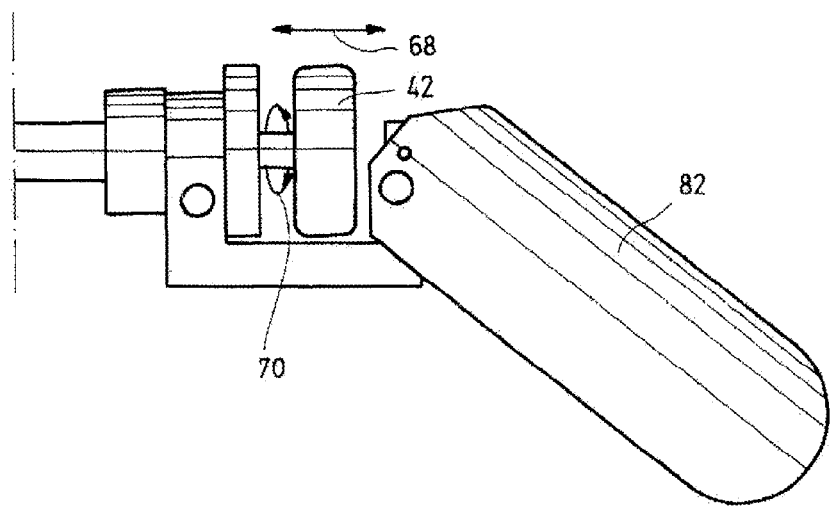
FIG. 3 shows the proximal portion of the instrument according to FIG. 1A, wherein a part of the handle is inclined with respect to the longitudinal extension of the instrument.

An arrow 68 in FIG. 3 shows the axial moveability of the operating element 42 and another double arrow 70 indicates the rotatability of the operating element 42. In order to transmit the rotational movement of the operating 42 to the jaw parts 28 and 30, the force transmission element 38 is also rotatable about the longitudinal axis 34. To this end, the force transmission element 38 is rotationally fixedly connected with the pivotable jaw part 30, and, thereby, with the jaw part 28.

It is to be understood that instead of being configured as an axially movable and rotatable knob, the operating element 42 can also be configured in the form of a scissor grip arrangement as known from conventional instruments, which are suited for achieving the desired motion of the force transmission element 38 and the jaw parts 28 and 130.

Figure 5A:
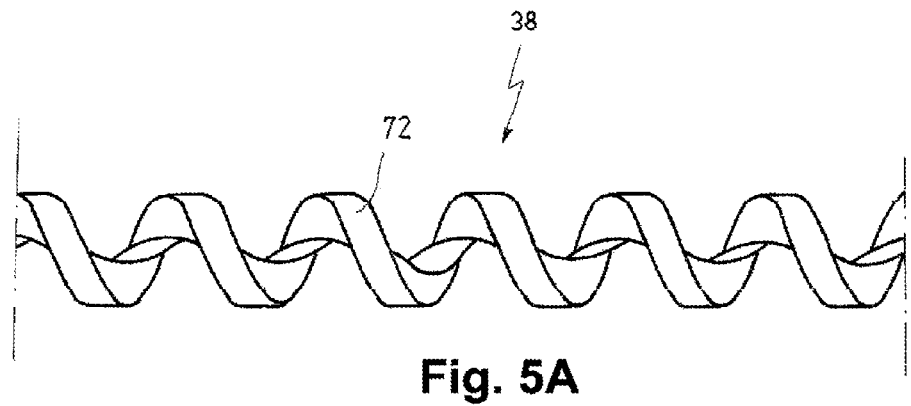
FIGS. 5A-5C show different embodiments of a force transmission element for use in the medical instrument according to FIGS. 1A through 4.

Instead of being configured as a thin push/pull rod, FIG. 5A shows an embodiment of the force transmission element 38 in form of a helix or coil 72. The helix or coil 72 has an improved ability to transmit torques for rotating the jaw parts 28 and 30 rather than a thin push/pull rod.

Figure 5B:
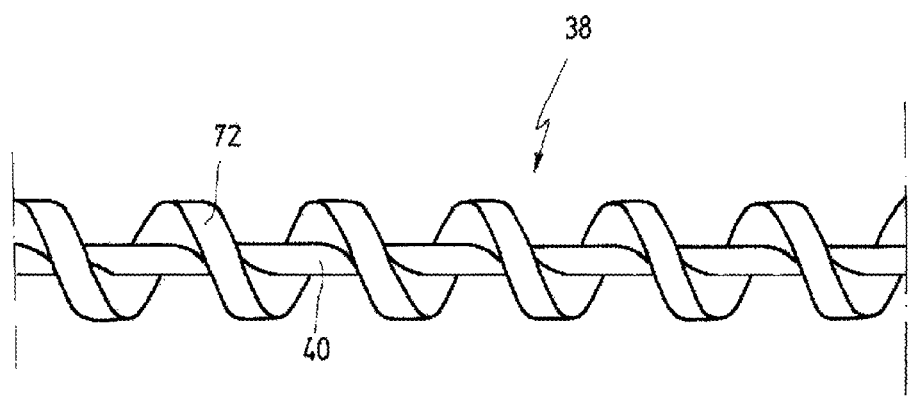

FIG. 5B shows an embodiment of the force transmission element 38 which comprises the helix or coil 72 which is cored by a push/pull rod 40. In particular, the helix or coil 72 is made in one piece with the push/pull rod 40. The force transmission element 38 has an improved ability to transmit push and pull forces due to the push/pull rod 40, and the helix 72 has the function of reliably transmit torques to the jaw parts 28 and 30.

Figure 5C:
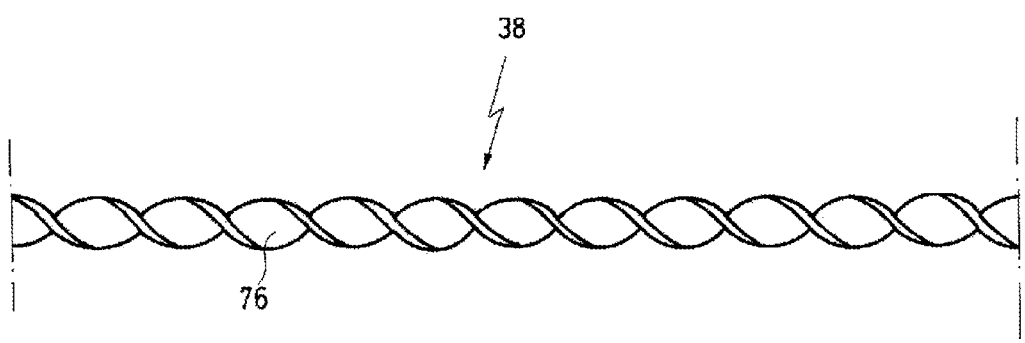

Another embodiment of the force transmission element 38 is shown in FIG. 5C. In this case, the force transmission element 38 is configured as a twisted strip 76 which is suited both for transmitting push and pull forces as well as torques. While twisted strip 76 is rectangular in cross-section in the shown embodiment, twisted strips of other cross-sectional shapes can be envisaged, for example twisted strips having a cross-section in form of a '+', etc.

As noted above, the distal end portion 20 of the shaft 18 is inclinable with respect to the main portion 22 of the shaft 18. In order to change the inclination angle of the distal end portion 20, which inclination angle can be varied by about 0° to about 90° in the preferred embodiment, a second operating element 78 is provided adjacent to the first operating element 42. The second operating element 78 preferably is a rotatable wheel or knob which is connected via a second force transmission element (not shown in this embodiment, but in another embodiment described below) via a gear wheel arrangement, for example, in order to transform a rotation of the second operating element 78 into an axial movement of the second force transmission element. The second force transmission element, in turn, is operatively connected with the distal end portion 20 in order to incline the distal end portion 20 with respect to the main portion 22 of the shaft 18. The second force transmission element can be arranged off-center with respect to the longitudinal center axis of the shaft 18.

According to another aspect of the instrument 10, the shaft 18 itself is rotatable with respect to the handle 16 about its longitudinal axis. The distal end portion 20 of the shaft 18 is rotatably fixed to the main portion 22 of the shaft 18. Thus, for a given inclination angle of the distal end portion 20 with respect to the main portion 22, the jaw parts 28 and 30 can be moved along a circular path around the longitudinal axis of the shaft 18. The jaw parts 28 and 30, in turn, are rotatable with respect to the longitudinal axis of the distal end portion 20 for any given inclination angle of the distal end portion 20 and for any given rotational position of the shaft 18 with respect to the handle 16. By rotating the jaw parts 28 and 30 with respect to the distal end portion 20, the object 36, for example a needle, can be oriented in any angular position at a surgical site.

A third operating element 80 is provided at the handle 16 which is configured as a rotatable wheel or knob connected with the shaft 18.

The handle 16 is designed for one-hand use. The handle 16 comprises an elongated bar 82 which can be held in the palm of the users hand. According to FIG. 3, the bar 82 of the handle 16 is inclinable with respect to the longitudinal direction of the shaft 18. In particular, the bar 82 can be fixed in a desired angular position with respect to the shaft 18.

The first operation element 42, the second operating element 78 and the third operating element 80 are arranged at the handle 16 in a serial order in longitudinal direction of the shaft 18 so that each of the operating elements 42, 78, 80 can be operated by the thumb or a finger of the same hand holding the bar 82.

Now, with respect to FIGS. 6 through 9, a preferred embodiment of a medical instrument 110 for grasping an object will be described. Those parts which are identical, similar or comparable with respective parts of the instrument 10, are referenced with the same reference numeral as in the instrument 10, raised by 100.

Figure 6:
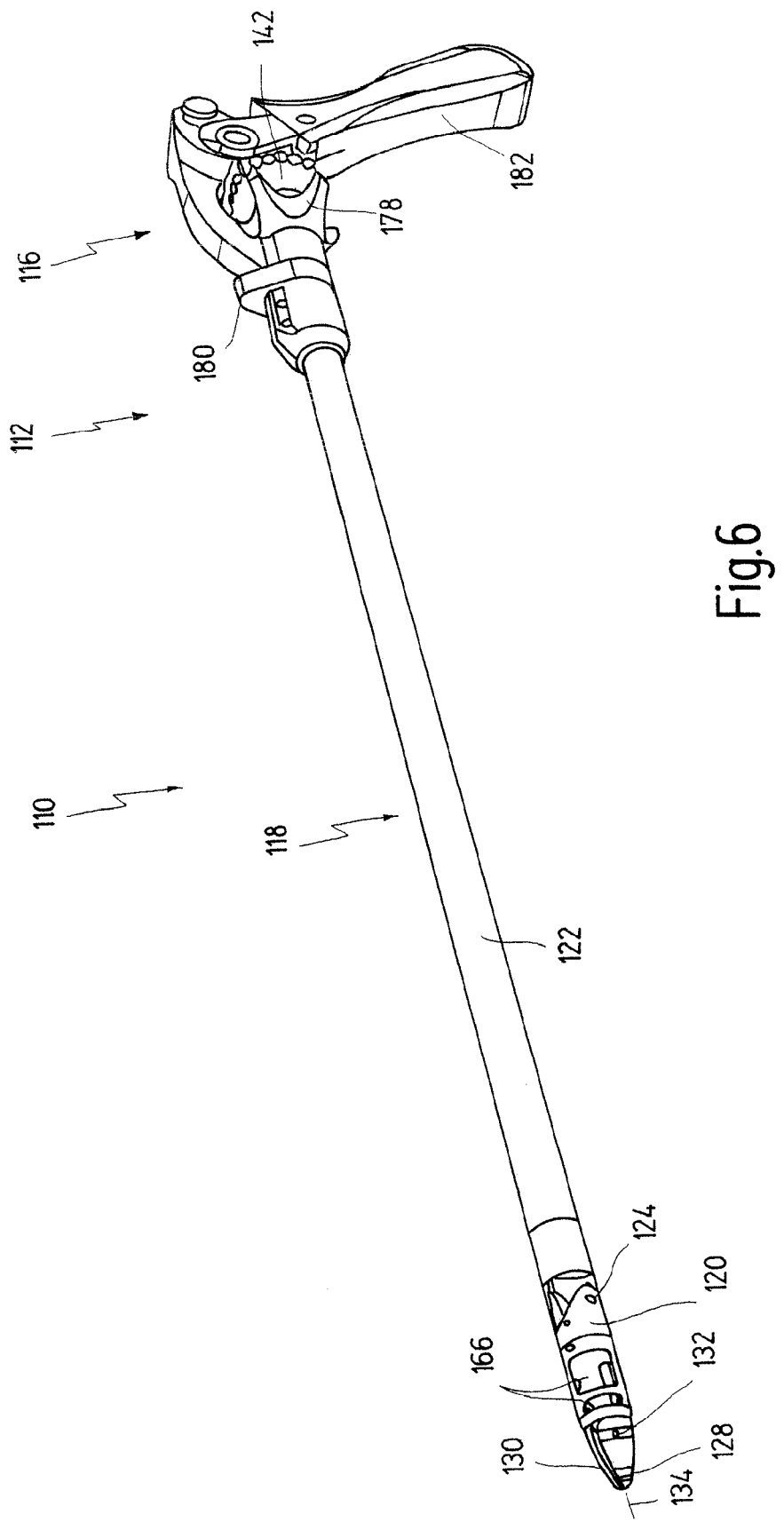
FIG. 6 shows another embodiment of a medical instrument for grasping an object in a perspective total view.
Figure 7:
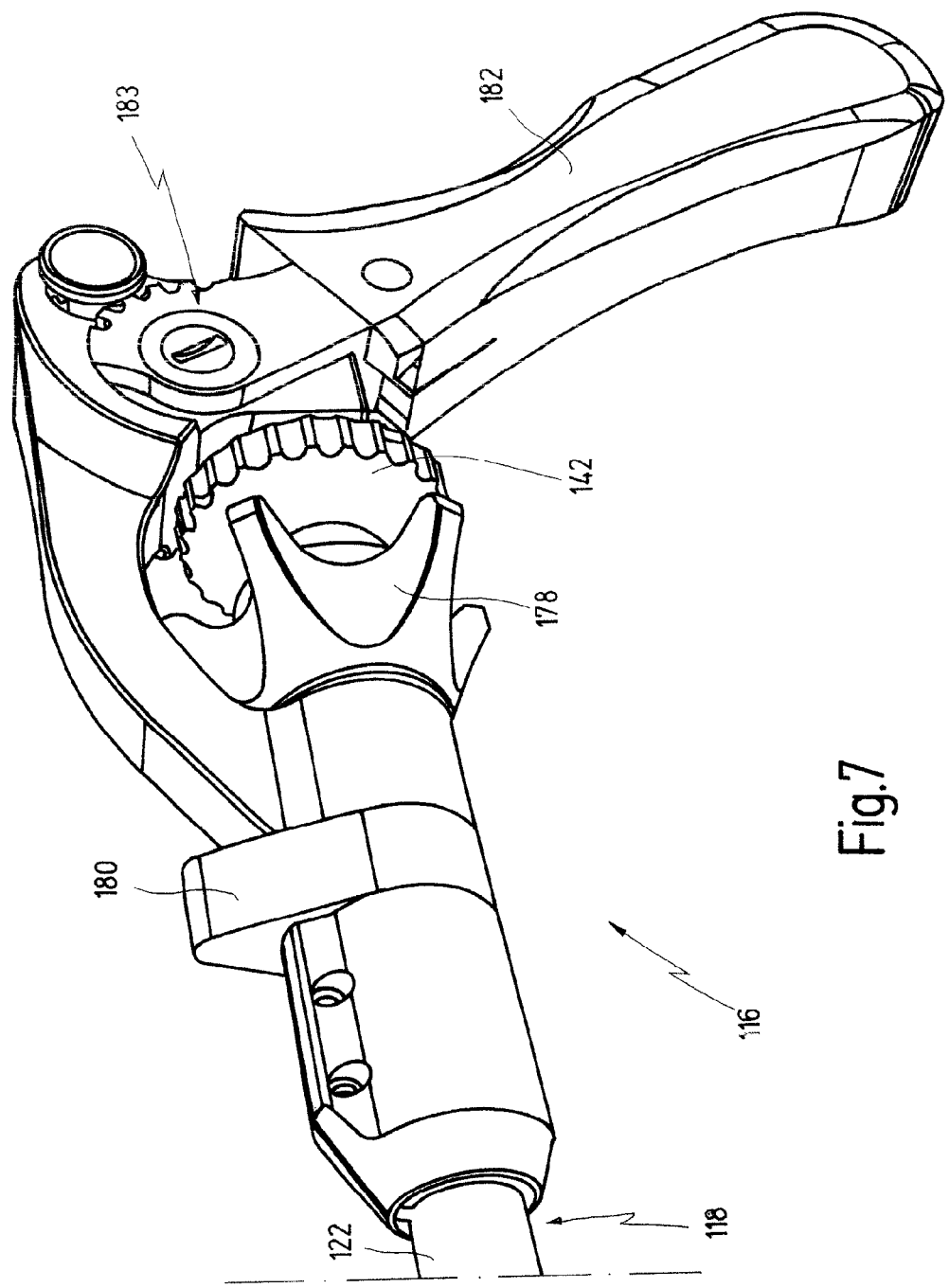
FIG. 7 shows a proximal portion of the instrument in FIG. 6 in a perspective view in an enlarged scale with respect to FIG. 6.
Figure 9A:
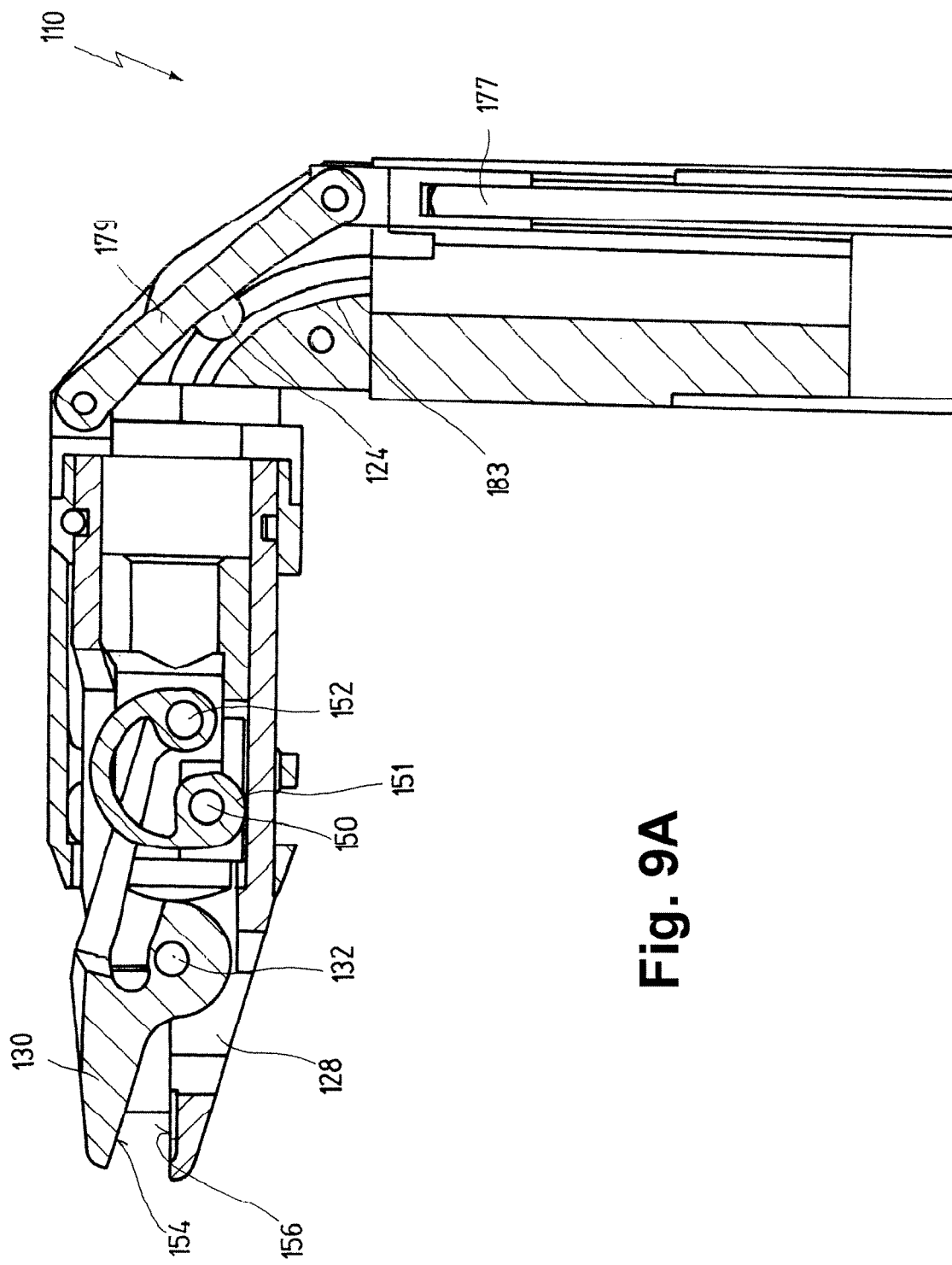
FIG. 9A-9C show the distal portion of the instrument according to FIG. 8 in another operating state with respect to FIG. 8 and in three different operating states of the pivotable jaw part.
Figure 9B:
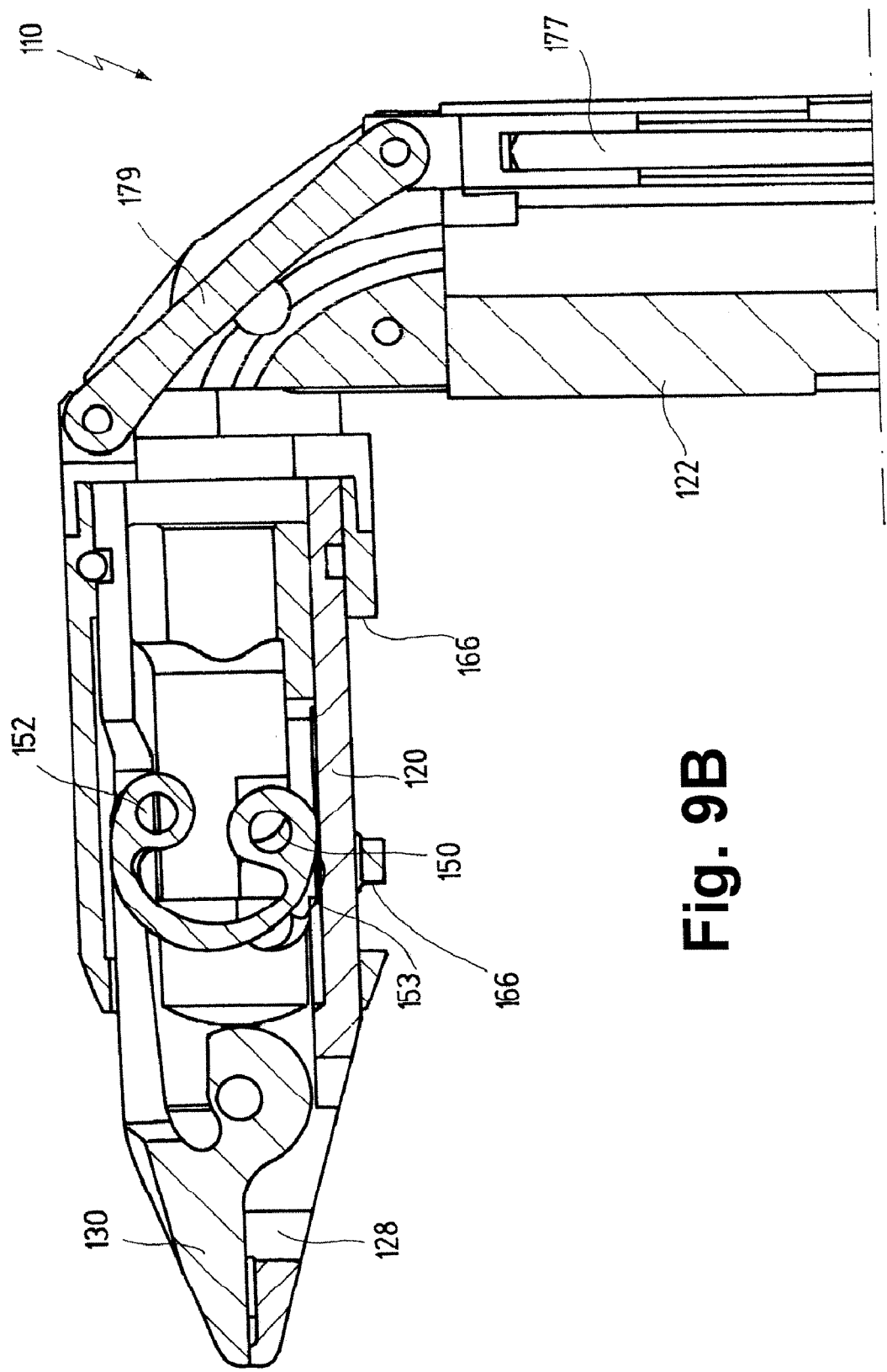
Figure 9C:
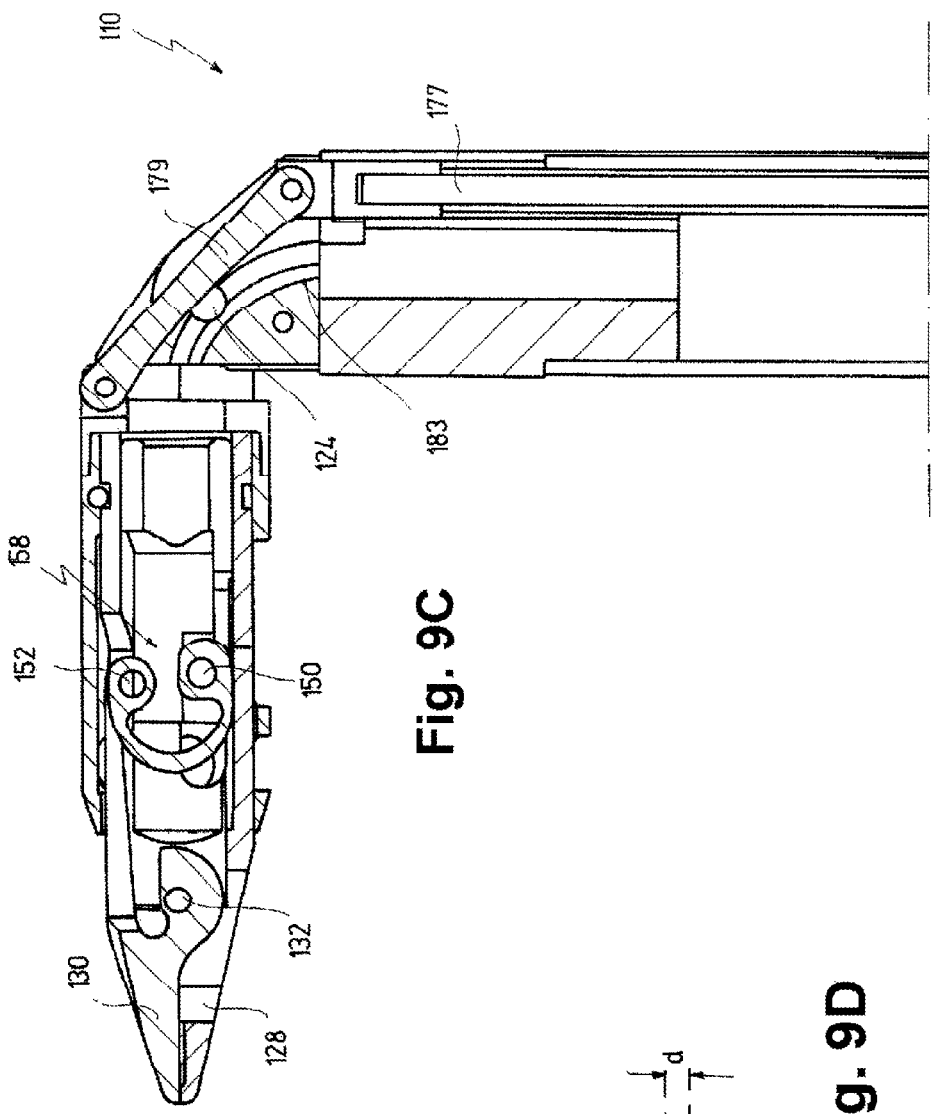

FIG. 6 shows the instrument 110 in its entirety. In a proximal portion 112, the instrument 110 comprises a handle 116, to which an elongated shaft 118 is connected. The shaft 118 comprises a distal end portion 120 in a distal portion 114 of the instrument 110, and a main portion 122. The distal end portion 120 and the main portion 122 are connected via an articulation 24 so that the distal end portion 120 can be inclined with respect to the main portion 122 as shown in FIGS. 9A through 9C.

At a distal end of the distal end portion 120, an immovable jaw part 128 and a movable jaw part 130 are arranged. The movable jaw part 130 is pivotable with respect to the immovable jaw part 128 via an articulation 132 as already described with respect to the jaw parts 28 and 30 of instrument 10.

The jaw parts 128 and 130 further are rotatable about a longitudinal axis 134.

Figure 8:
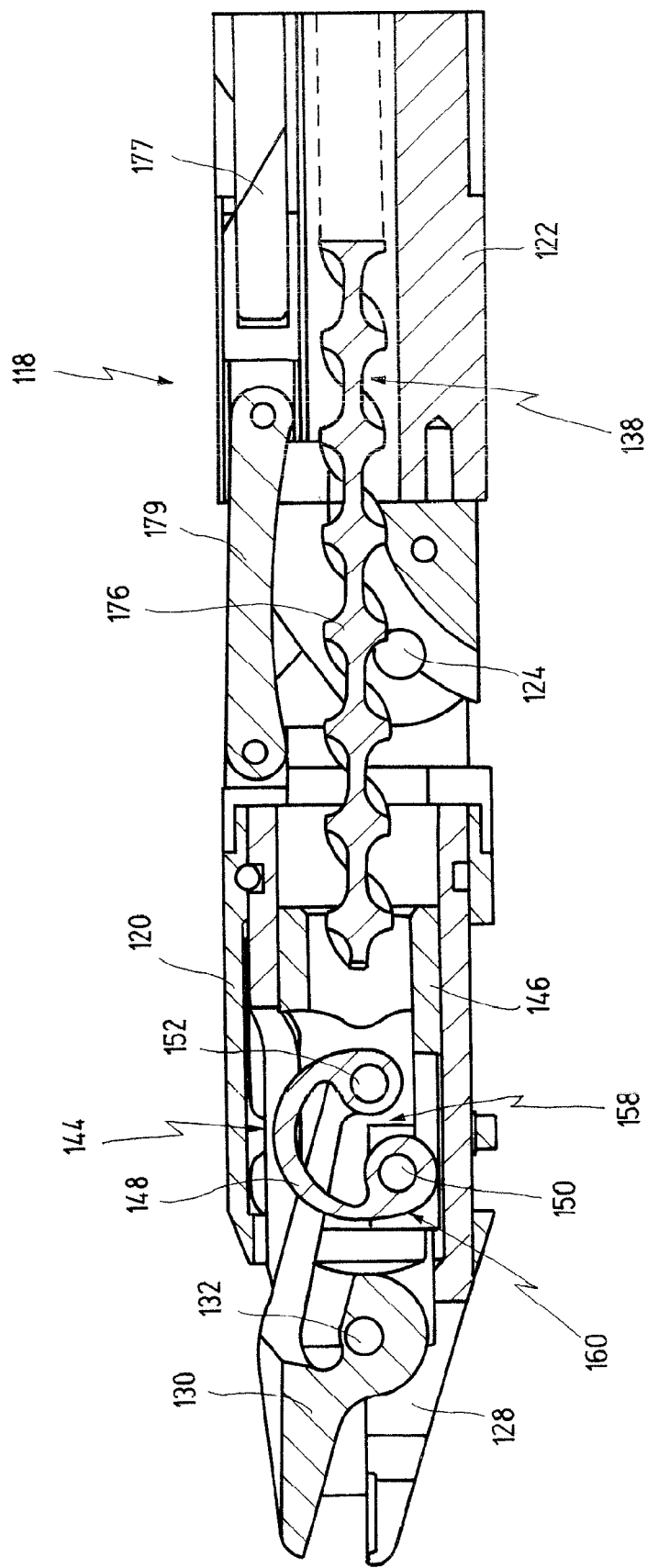
FIG. 8 shows a distal portion of the instrument in FIGS. 6 and 7 in a longitudinal section in a first operating state.

For opening and closing the pivotable jaw part 130 with respect to the immovable jaw part 128 between a grasp state and a release state as described with respect to the instrument 10, a force transmission element 138, shown in FIG. 8, extends in longitudinal direction through the shaft 118. The force transmission element 138 is configured as a twisted strip 176 at least in the portion of connection between the distal end portion 120 and the main portion 122 of the shaft 118 as shown in FIG. 8. It is to be understood that the force transmission element 138 can be configured in its entirety as the twisted strip 176 as indicated by broken lines in FIG. 8. As an alternative, the force transmission element 138 can be configured as a push/pull rod in its proximal portion which extends to an operating element 142 shown in FIG. 7. The operating element 142, again, is configured as an axially movable and rotatable wheel or knob arranged at the handle 116. Nevertheless, other arrangements of the operating element 142, like scissor handles can be envisaged for the operating element 142.

A distal end portion 146 of the force transmission element 138 is connected with the pivotable jaw part 130 via au articulated joint 144. The articulated joint 144 comprises a lever 148. The force transmission element 138, i.e. the distal end portion 146 of the force transmission element 138, is articulatedly connected with the lever 148 at a first location 150 forming a first end of the lever 148, and a second end of the lever 148 is articulatedly connected with the pivotable jaw part 130 at a second location 152. In the release state of the pivotable jaw part 130, the first location 150 is positioned distally from the second location 152 as shown in FIGS. 8 and 9A.

For immobilizing the pivotable jaw part 130 in the grasp state, a latching mechanism 158 is provided comprising a latching element 160 again arranged in the region of the force transmission from the transmission element 138 to the pivotable jaw part 130 which, when the force transmission element 138 is further axially moved beyond the position in which the grasped state is reached (FIG. 9B), changes into an over-centre stable state (FIG. 9C). In the present embodiment, the latching element 160 forms part of the articulated joint 144 and, in particular, is formed by the lever 148 itself. The lever 148, accordingly, is configured as elastically deformable element, which in the present embodiment, is configured in arch-shape, in particular in about C-shape. The first and second locations 150 and 152 which form the articulation locations between the lever 148 and the pivotable jaw part 130 and the force transmission element 138 are arranged at the end of the arch or C.

FIG. 8 shows the pivotable jaw part 130 in its open state where the first location 150 is arranged distally from the second location 152. By moving the operating element 142 in proximal direction, the force transmission element 138 pulls the first location 150 in proximal direction and thereby the movable jaw part 130 pivots about the articulation 132 towards the immovable jaw part 128. In case that no object is positioned between the jaw parts 128 and 130, axial movement of the force transmission element 138 in proximal direction will cause the pivotable jaw part 130 to close onto the immovable jaw part 128 as shown in FIG. 9B. In the instant when the pivotable jaw part 130 closes onto the immovable jaw part 128, the first location is still positioned distally from the second location 152 as shown in FIG. 9B. A further axial movement of the force transmission element 138 (by further actuating the operating element 142 in proximal direction) causes an over-centre-movement of the lever 148 which, in turn, causes the lever 148 as the latching element 160 to snap into a latched stable state in which a surface 153 of the lever 148 approximately runs parallel to the longitudinal direction of the distal end portion 120 of the shaft 118. It is to be noted that in FIGS. 9A through 9C, the force transmission element except of the distal end portion 146 of the force transmission element 138 has been omitted for the sake of simplicity of the drawing.

Figure 9D:
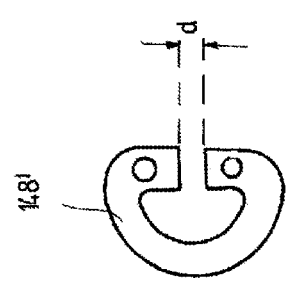
FIG. 9D shows an element of a latching mechanism in an embodiment modified with respect to the embodiment in FIGS. 9A-9C.

FIG. 9D shows a modified embodiment of the arc-shaped lever 148 which is referenced with 148'. Differently from the lever 148, the free distance between the facing open ends of the lever 148' is limited to a distance d of, for example, a few millimetres, for example about 3 to 4 mm, so that the spring travel of the lever 148' is limited to the distance d.

Figure 10A:
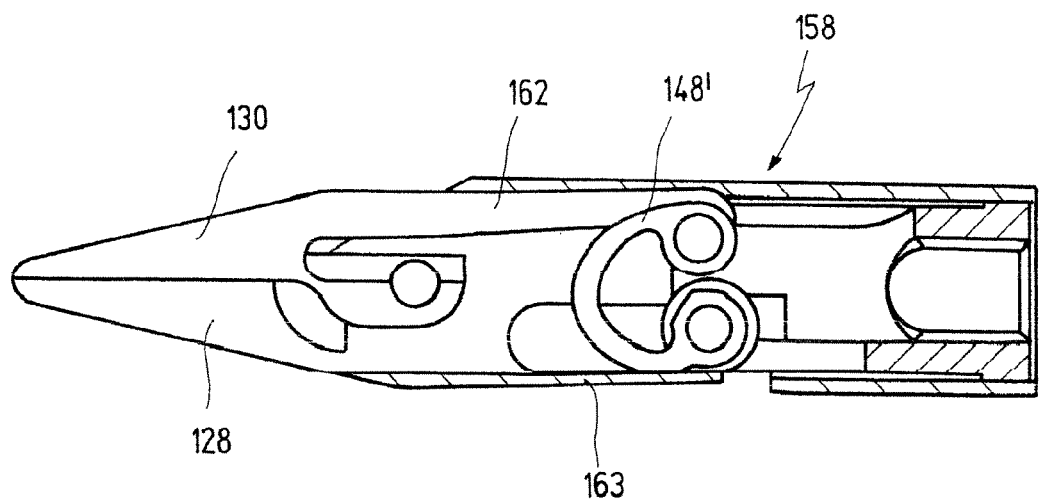
FIGS. 10A and 10B show another embodiment similar to the embodiment of FIGS. 6-9C using the element shown in FIG. 9D.
Figure 10B:
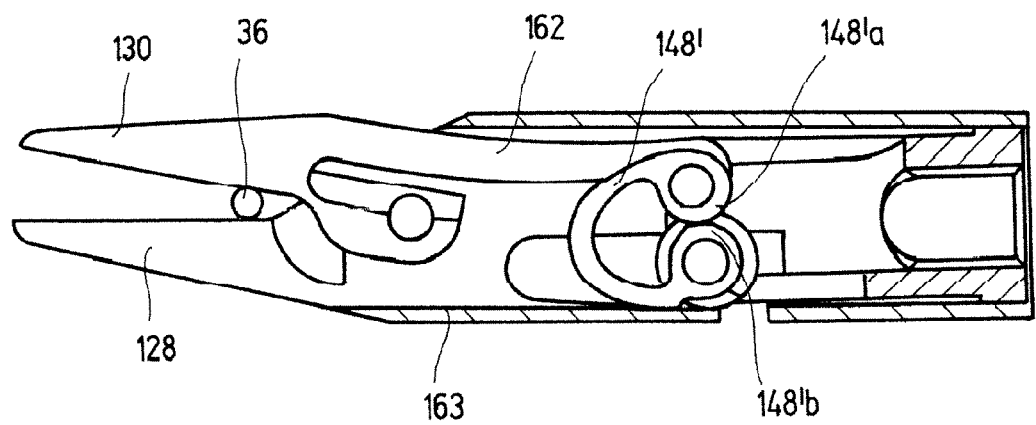

FIGS. 10A and 10B show the distal end of the instrument 110, wherein, instead of the lever 148, the lever 148' is used as a latching element of the latching mechanism 158. In particular, FIG. 10B shows the latched state of the latching mechanism 158, where the facing ends 148'a and 148'b contact each other and act as a stop. In order to securely hold the jaw part 130 in the grasp state, in particular if an object, for example a needle 36 shall be securely held between the jaw parts 128 and 130, a further element of the latching mechanism 158 should contribute to the latching, which is realised by a flexible design of the proximal portion 162 of the moveable jaw part 130. When the needle 36 is gripped between the jaw parts 128, 130, first the lever 148' will deform, for example by 0.3 mm until the facing ends 148'a and 148'b meet. Further closure of the jaw parts 128 and 130 will result in equal deformation of the proximal end portion 162 of the jaw parts 130. Optionally, a further latching element of the latching mechanism 158 can contribute to the latching action, namely a flexible element 163 against which the lever 148' abuts, and which is deflected from the state shown in FIG. 10A to the state shown in FIG. 10B.

FIG. 10A shows the "normal" closed position of the jaw parts 128 and 130 without an object or only a thin object like a thread being grasped between the jaw parts 128, 130. In this "normal" closed position, there is only little or no deformation of the proximal end portion 162 and/or the flexible element 163.

The advantage of the limited spring travel of the lever 148' is that the lever 148' is less subject to the risk of breaking after a high number of load cycles.

Like shown in FIG. 2B, lever 148 can be equipped with a wheel to reduce friction, and a recess can be provided in part 120 in which the part 151 or the wheel, if provided, can snap so that a tactile feed back to the user is provided for the latched position.

For releasing the latched state of the pivotable jaw part 130, the operating element 142 has to be moved in distal direction as already described with respect to the instrument 10.

The lever 148 as the latching member confers varying mechanical advantage in the mechanism as it rotates. At the beginning of the action the mechanical advantage is low, so the force applied to the jaw parts 128, 130 is low, but the jaw part 130 rotates through a relatively large angle for just a small movement of the knob 142. As the lever 148 reaches the over-centre-position the mechanical advantage is very large, so the jaw parts 128, 130 grip very forcefully although little force is required at the knob 142. This provides a useful way of minimizing the range-of-motion of the knob 142 while providing a forceful action when it is required—that is, when the jaw parts 128, 130 are closing on an object, for example a needle.

For enhancing the functional safety of the instrument 110, the distal end portion 120 of the shaft 118 comprises two windows 166 as shown in FIG. 6.

It is to be noted that the different embodiments of the force transmission element 38 in FIGS. 5A through 5C can also be used in the instrument 110 instead of the force transmission element 138.

FIGS. 8 and 9 additionally show a second force transmission element 177 for inclining the distal end portion 120 with respect to the main portion 122 of the shaft 118. The second force transmission element 177 is connected with a lever 179 which causes the distal end portion 120 to incline with respect to the main portion 122 when the force transmission element 177 is axially moved in distal direction. The second force transmission element 177 is connected with a second operating element 178 arranged at the handle distally form the first operating element 142. The second operating element 178 is configured as a rotatable knob which is connected with the second force transmission 177 via a gear arrangement, for example. As can be seen in FIG. 8, the force transmission element 177 extends through the shaft 118 eccentrically with respect to the longitudinal center axis of the shaft 118.

It goes without saying that the force transmission element 138 is flexible at least in the region of the articulation 124. Furthermore, a central longitudinal axis of the force transmission element is positioned such that it coincides with the center of the articulation 124.

This arrangement ensures that the path which the force transmission element 138 follows does not change in length when the distal end portion 120 is inclined with respect to the main portion 122. A guide 179 is provided for ensuring proper alignment of the force transmission element 138 with respect to the articulation 124 mentioned before.

Further, the shaft 118 is rotatable about the longitudinal axis 134 as already described with respect to the shaft 18 of the instrument 10 above. For rotating the shaft 118, a third operating element 180 is provided at the handle 116 (FIG. 6).

The handle 116 further comprises a bar 182 which can be inclined with respect to the shaft 118 in a range of angles between 0° and about 90°, wherein the bar 182 forms an angle of about 80° with respect to the shaft 118 in FIG. 6. The operating elements 142, 178 and 180 are arranged such that all operating elements 142, 178 and 180 can be operated by the thumb or finger of the same hand holding the bar 182. Thus, the instrument 110 is also suited for one-hand operation.

The bar 182 of the handle 116 or the bar 82 of the handle 16 preferably are not only inclinable in the plane which includes the longitudinal axis of the shaft, but also in a plane perpendicular thereto, in order to allow the user to move his or her hands closer or further from the operating elements. Thus, the user can adjust the handle 16 or 116 in a position which is comfortable.

All possible degrees of freedom of the jaw parts 28 and 30 described above with respect to the instrument 10, are also given for the jaw parts 128 and 130 by the rotatability of the shaft 118 and the inclineability of the distal end portion 120 with respect to the main portion 122 of the shaft 118. Also, all functions described with respect to the instrument 10 and not fully described with respect to the instrument 110, are also present in the instrument 110.

The invention claimed is:

1. A medical instrument for grasping an object, comprising an elongated shaft having a distal end and a proximal end,
two jaw parts arranged at said distal end of said shaft, at least one of said two jaw parts being pivotable with respect to the other of said two jaw parts between a grasp state for grasping said object between said two jaw parts and a release state for releasing said object,
a handle arranged at said proximal end of said shaft and having at least one operating element for moving said at least one pivotable jaw part between said grasp state and said release state,
an axially movable force transmission element having a first end operatively connected with said at least one operating element, and a second end connected with said at least one pivotable jaw part via an articulated joint,
a latching mechanism for immobilizing said at least one pivotable jaw part in said grasp state, said latching mechanism comprising at least one latching element arranged in the region of the force transmission from said force transmission element to said at least one pivotable jaw part which, when said force transmission element is further axially moved beyond a position in which said grasp state is reached, changes into an over-center stable state.

2. The instrument of claim 1, wherein said at least one latching element is elastically deformable and changes into said over-center stable state via a deformed state.

3. The instrument of claim 1, wherein said at least one latching element forms at least part of one of said articulated joint, a proximal portion of said at least one movable jaw part, said distal end of said force transmission element.

4. The instrument of claim 1, wherein said at least one latching element changes into an unlatched state when said force transmission element is moved back beyond a position in which said grasp state is reached.

5. The instrument of claim 1, wherein said articulated joint comprises a lever one end of which is articulatedly connected with said force transmission element at a first location, and the other end of which is articulatedly connected with said at least one pivotable jaw part at a second location which is spaced apart from said first location in direction transverse to a direction of axial movement of said force transmission element, wherein, in said release state, one of said first and second locations is positioned distally from the other location, and said latching element changes into said stable state, when the location which is the distal one in said release state moves in a position which is proximally from the other location, or vice versa, respectively.

6. The instrument of claim 5, wherein said lever of said articulated joint forms said latching element.

7. The instrument of claim 6, wherein said lever is configured in arch-shape, said first and second locations of said articulated connection with said force transmission element and said at least one movable jaw part being arranged at least approximately at ends of the arch.

8. The instrument of claim 1, wherein a proximal portion of said at least one movable jaw part forms said latching element and is elastically deformable.

9. The instrument of claim 1, wherein said jaw parts are rotatable relative to said shaft about a longitudinal axis of said shaft.

10. The instrument of claim 9, wherein said force transmission element further is rotatable about a longitudinal axis of said force transmission element and rotationally fixedly connected with said at least one pivotable jaw part.

11. The instrument of claim 1, wherein the instrument is a needle holder.

12. A medical instrument for grasping an object, comprising
an elongated shaft having a distal end and a proximal end,
two jaw parts arranged at said distal end of said shaft, at least one of said two jaw parts being pivotable with respect to the other of said two jaw parts between a grasp state for grasping said object between said two jaw parts and a release state for releasing said object,
a handle arranged at said proximal end of said shaft and having at least one operating element for moving said at least one pivotable jaw part between said grasp state and said release state,
an axially movable force transmission element having a first end operatively connected with said at least one operating element, and a second end connected with said at least one pivotable jaw part via an articulated joint,
a latching mechanism for immobilizing said at least one pivotable jaw part in said grasp state,
said jaw parts being rotatable relative to said shaft about a longitudinal axis of said shaft, and said force transmission element further being rotatable about a longitudinal axis of said force transmission element and rotationally fixedly connected with said at least one pivotable jaw part.

13. The instrument of claim 12, wherein said force transmission element comprises a helix.

14. The instrument of claim 13, wherein said helix does not lengthen when transmitting pull forces and does not shorten when transmitting push forces.

15. The instrument of claim 13, wherein said helix is configured as a twisted strip.

16. The instrument of claim 12, wherein said force transmission element comprises a push/pull rod.

17. The instrument of claim 12, wherein said force transmission element comprises a helix which is cored with a push/pull rod.

18. The instrument of claim 17, wherein said push/pull rod is made in one piece with said helix.

19. The instrument of claim 12, wherein said at least one operating element is movable in longitudinal direction of said shaft for axially moving said force transmission element.

20. The instrument of claim 12, wherein said at least one operating element is rotatable about a longitudinal direction of said shaft for rotating said force transmission element.

21. The instrument of claim 12, wherein said shaft has a distal end portion and a main portion, wherein said jaw parts are arranged at said distal end portion, and said distal end portion is inclinable with respect to said main portion of said shaft.

22. The instrument of claim 21, wherein said main portion of said shaft is rotatably fixed to said distal end portion of said shaft.

23. The instrument of claim 21, wherein said jaw parts are rotatable about a longitudinal direction of said distal end portion relative to said distal end portion.

24. The instrument of claim 23, wherein a second axially movable force transmission element is provided which is operatively connected with said distal end portion of said shaft and with a second operating element arranged at said handle.

25. The instrument of claim 12, wherein said shaft is rotatable about a longitudinal axis of said shaft.

26. The instrument of claim 25, wherein a third operating element is arranged at said handle for rotating said shaft.

27. The instrument of claim 12, wherein said handle comprises an elongated bar.

28. The instrument of claim 27, wherein said bar is inclinable with respect to a longitudinal direction of said shaft.

29. The instrument of claim 27, wherein said bar is inclinable with respect to said shaft in a direction oblique or perpendicular to a longitudinal direction of said shaft.

30. The instrument of claim 12, wherein said latching mechanism comprising at least one latching element arranged in the region of the force transmission from said force transmission element to said at least one pivotable jaw part which, when said force transmission element is further axially moved beyond a position in which said grasp state is reached, changes into an over-center stable state.

31. The medical instrument of claim 12, wherein said instrument is a needle holder.

* * * * *